(12) United States Patent
Wolff et al.

(10) Patent No.: US 11,322,243 B2
(45) Date of Patent: May 3, 2022

(54) METHOD AND SYSTEM FOR IDENTIFYING AND DISPLAYING MEDICAL IMAGES

(71) Applicant: NeoSoft, LLC, Pewaukee, WI (US)

(72) Inventors: Steven D. Wolff, New York, NY (US); Steven H. Schmidt, Cedarburg, WI (US)

(73) Assignee: NeoSoft, LLC, Pewaukee, WI (US)

( * ) Notice: Subject to any disclaimer, the term of this patent is extended or adjusted under 35 U.S.C. 154(b) by 89 days.

(21) Appl. No.: 16/856,290

(22) Filed: Apr. 23, 2020

(65) Prior Publication Data

US 2021/0118548 A1 Apr. 22, 2021

Related U.S. Application Data

(60) Provisional application No. 62/923,061, filed on Oct. 18, 2019.

(51) Int. Cl.
| | |
|---|---|
| *G06K 9/00* | (2006.01) |
| *G16H 30/20* | (2018.01) |
| *G06T 7/00* | (2017.01) |
| *A61B 5/00* | (2006.01) |
| *G06T 7/11* | (2017.01) |

(52) U.S. Cl.
CPC .............. *G16H 30/20* (2018.01); *A61B 5/743* (2013.01); *A61B 5/748* (2013.01); *G06T 7/0014* (2013.01); *G06T 7/11* (2017.01); *G06T 2207/10088* (2013.01)

(58) Field of Classification Search
CPC ......... A61B 5/743; G06T 7/0014; G06T 7/11; G16H 30/20
See application file for complete search history.

(56) References Cited

U.S. PATENT DOCUMENTS

| | | | |
|---|---|---|---|
| 7,787,672 B2 | 8/2010 | Reicher et al. | |
| 8,094,901 B1 | 1/2012 | Reicher et al. | |
| 8,280,129 B2 | 10/2012 | Futami et al. | |
| 8,386,273 B2 | 2/2013 | Kaminaga et al. | |
| 8,610,746 B2 | 12/2013 | Fram et al. | |
| 8,634,598 B2 * | 1/2014 | Hyde | H04N 7/18 382/115 |
| 9,131,913 B2 * | 9/2015 | Sehnert | G16H 30/20 |
| 9,471,210 B1 | 10/2016 | Fram et al. | |
| 9,501,863 B1 | 11/2016 | Fram et al. | |

(Continued)

*Primary Examiner* — Hadi Akhavannik
(74) *Attorney, Agent, or Firm* — Boyle Fredrickson, SC (57) ABSTRACT

An improved method and system for identifying and displaying related images obtained during an examination is disclosed. Each image includes both pixel data, corresponding to the image to be displayed, and location information, defining a relationship between the pixel data and a reference point. During a review of the images, a physician may identify an abnormality or particular region of interest in one image. The location information corresponding to the position identified by the physician within the image is obtained from the image file. Having identified location information for a particular location on the first image, the system analyzes the location information corresponding to the pixel data for each of the other stored images to identify any other image that intersects the identified location. All images that intersect the identified location may then be displayed adjacent to the first image for inspection by the physician.

13 Claims, 8 Drawing Sheets

(56) References Cited

U.S. PATENT DOCUMENTS

| | | | |
|---|---|---|---|
| 9,566,044 B2* | 2/2017 | Ando | G06T 19/003 |
| 10,055,543 B2* | 8/2018 | Kozuka | G06F 16/50 |
| 10,096,111 B2 | 10/2018 | Fram et al. | |
| 10,349,915 B2 | 7/2019 | Xu et al. | |
| 10,413,253 B2 | 9/2019 | Oh et al. | |
| 10,417,737 B2 | 9/2019 | Park et al. | |
| 10,429,472 B2 | 10/2019 | Tatebayashi | |
| 10,709,408 B2* | 7/2020 | Saito | A61B 6/06 |
| 10,726,295 B2* | 7/2020 | Takata | A61B 6/5217 |
| 2009/0093706 A1* | 4/2009 | Zhang | A61B 5/055 |
| | | | 600/410 |
| 2010/0138240 A1* | 6/2010 | Leib | G16H 50/20 |
| | | | 705/3 |
| 2018/0055468 A1* | 3/2018 | Reicher | A61B 6/468 |
| 2018/0122067 A1* | 5/2018 | Reicher | A61B 6/463 |
| 2018/0225824 A1 | 8/2018 | Fram et al. | |
| 2019/0287245 A1 | 9/2019 | Shiroishi et al. | |

* cited by examiner

METHOD AND SYSTEM FOR IDENTIFYING AND DISPLAYING MEDICAL IMAGES

CROSS-REFERENCE TO RELATED APPLICATIONS

This application claims priority to U.S. Provisional Application Ser. No. 62/923,061, filed Oct. 18, 2019, the entire contents of which is incorporated herein by reference

BACKGROUND OF THE INVENTION

The subject matter disclosed herein relates to a method and system for identifying images generated during medical imaging for display and, more specifically, to identifying a location of interest on a first medical image and automatically identifying other medical images that include the same location.

As is known to those skilled in the art, medical images are commonly used to diagnose and treat patients without the use of invasive procedures. Various technologies exist for medical imaging, such as X-ray, ultrasound, computer tomography (CT), positron-emission tomography (PET), and magnetic resonance imaging (MRI) technologies. A different technology may be selected to perform a desired examination according to the anatomical region to be imaged. For example, an X-ray machine may be selected to perform imaging of the skeletal system while an MRI scanner may be selected to perform imaging of soft-tissue or organs within a patient.

As is also known in the art, the number of images obtained for the different technologies may vary widely for a single examination. When an x-ray is required, the technician may obtain two or three images from different angles or with the target anatomy oriented in different positions. The number of images is, however, limited due to concerns about side effects of radiation received by the patient while receiving the x-rays. In contrast, an examination performed with an MRI scanner may involve hundreds or thousands of images. An MRI scanner generates a strong magnetic field which aligns nuclei in the presence of the magnetic field and then detects the faint nuclear magnetic resonance (NMR) signals given off by nuclei returning to a normal state in the absence of the magnetic field. Because the magnetic field generated by an MRI scanner does not present undesirable radiation exposure to a patient, the number of images taken during an examination on an MRI scanner is not limited in the same manner as for an X-ray machine.

During an examination with an MRI scanner, it is often desirable to perform multiple scans of a patient where one or more parameters are changed between scans. The parameters may relate, for example, to image resolution such as pixel resolution, thickness of a slice, or field of view; to the anatomical region being imaged such as the orientation of the anatomical region (e.g., axial, sagittal, or coronal); or to the pulse sequence of the scan such as the repetition time (TR), the echo time (TE), or the flip angle. In each scan, multiple two-dimensional (2D) images, or slices, may be taken of a three-dimensional (3D) region of interest. The set of images may be stored as a series on the scanner or on an external computer for subsequent analysis and review. Each series may include just a few images (e.g. 10 or less) or up to hundreds of images. Further, an examination may require tens of different series. The complete examination, therefore, can result in thousands of images.

In order to provide a complete diagnosis for a patient, a technician is required to review all of the images obtained during an examination. Reviewing such a large number of images is not without certain drawbacks. A technician may identify an area of interest, such as an anomaly, in a first image that is stored within one of the series. It may be desirable to review the same area of interest from other scans which were taken using a different set of scanning parameters or which were taken at a different orientation. However, there is presently no option for a technician to know in which scan the particular area of interest may be located or to readily identify other images that may show the anomaly. The technician has the option to close one series and open a second series or even to open multiple series in tandem. However, the technician is required to review each image in the other series to identify whether the same area of interest is shown in one or more of the other series and only then is able to display the initial image and the image from the other series at the same time for analysis. The process is time consuming and may result in a technician not identifying one or more related images from different series that each identify the same region of interest.

Thus, it would be desirable to provide an improved method and system for identifying and displaying additional images containing a location identified on a first image.

BRIEF DESCRIPTION OF THE INVENTION

The subject matter disclosed herein describes an improved method and system for identifying and displaying additional images containing a location identified on a first image. The images are obtained during an examination and initially stored within different series, where each series may have just a few images or may include hundreds of images, Each image includes both pixel data, corresponding to the image to be displayed, and location information, defining a relationship between the pixel data and a reference point. Each series of images may correspond to a single scan, where different scans may utilize, for example, different imaging parameters or be taken along different planes of the anatomical region being imaged. During a review of the images, a physician may identify an abnormality or particular region of interest in one image. The physician selects the location of the abnormality or region of interest on the first image via a suitable user interface, such as a cursor and mouse or via a touchscreen. The location information corresponding to the position selected within the image by the physician is obtained from the image file. Having identified location information for a particular location on the first image, the system analyzes the location information corresponding to the pixel data for each of the other images within the present series and within each of the other series to identify any other image that intersects the identified location. All images that intersect the identified location may then be displayed adjacent to the first image for inspection by the physician.

According to one embodiment of the invention, a method for displaying images obtained from a magnetic resonance imaging (MRI) scanner is disclosed. A first image of an anatomical region obtained from the MRI scanner is displayed on a display device. An input is received at a processor from a user interface, where the input defines a position within the first image. A data set is read from a storage device in communication with the processor, where the data set corresponds to the first image and the data set includes coordinate information for a location of the anatomical region during imaging. The location for the anatomical region during imaging is determined from the data set that corresponds to the position within the first image defined by the input, and at least one additional image of the anatomical region, which includes the location of the anatomical region that corresponds to the position within the first image, is identified.

According to one aspect of the invention, the data set may be stored within an image file for the first image. Each additional image may be stored in an additional image file, and each additional image file may include coordinate information for the corresponding additional image. The step of identifying the at least one additional image of the anatomical region may also include the steps of reading the coordinate information from each additional image file, comparing the location of the anatomical region that corresponds to the position within the first image to the coordinate information from each additional image file, and identifying the at least one additional image when the coordinate information from a corresponding additional image file includes the location of the anatomical region that corresponds to the position within the first image.

According to another aspect of the invention, the first image may be stored in an image file and the data set may be stored within a separate file from the image file. Each additional image may be stored in an additional image file, and the separate file may include coordinate information for each additional image. The step of identifying the at least one additional image of the anatomical region may also include the steps of reading the coordinate information from the separate file for each additional image, comparing the location of the anatomical region which corresponds to the position within the first image to the coordinate information for each additional image, and identifying the at least one additional image when the coordinate information for an additional image includes the location of the anatomical region which corresponds to the position within the first image.

According to another embodiment of the invention, a system for displaying images obtained from a magnetic resonance imaging (MRI) scanner is disclosed. The system includes a storage device, a display device, a user interface, and a processor. The storage device is configured to store multiple images of an anatomical region obtained from the MRI scanner and a data set corresponding to the images. The display device is configured to selectively show each of the images. The user interface is configured to generate a signal corresponding to a position within a first image shown on the display device, where the first image is selected from the images. The processor is operative to receive the signal from the user interface and, responsive to receiving the signal, the processor is further operative to read the data set from the storage device, where the data set includes coordinate information for a location of the anatomical region during imaging for each of the images. The processor is further operative to determine the location for the anatomical region during imaging from the data set that corresponds to the position within the first image defined by the input and to identify at least one additional image of the anatomical region which includes the location of the anatomical region that corresponds to the position within the first image, where the at least one additional image is selected from the multiple images.

According to another aspect of the invention each additional image may be displayed on the display device with the first image. Optionally, a list of each additional image identified may be displayed on the display device.

According to still another embodiment of the invention, a method for displaying images obtained from a magnetic resonance imaging (MRI) scanner is disclosed. Pixel data is read from a first image file and displayed on a display device, where the first image file corresponds to an anatomical region being imaged by the MRI scanner. A pixel is selected from the pixel data displayed on the display device via a user interface, where the pixel defines a region of interest. Position information, which defines a location of the pixel data with respect to a reference coordinate system, is read from the first image file and used to determine the location of the pixel within the reference coordinate system. At least one additional image file having pixel data that corresponds to the location of the region of interest is identified. The position information may include an image origin and an orientation of the pixel data within the reference coordinate system.

According to still another aspect of the invention, the step of determining the location of the pixel within the reference coordinate system further includes the steps of determining an offset of the pixel within the pixel data from the image origin as a function of the orientation of the pixel data within the referent coordinate system and adding the offset to the image origin to determine the location of the pixel.

According to yet another aspect of the invention, each additional image file includes pixel data and position information corresponding to an additional image, Optionally, the orientation of the first image file and the orientation of the at least one additional image file may indicate that the pixel data in the first image file is in a first plane parallel to a second plane, where the second plane includes the pixel data in the second image. When the first plane is parallel to the second plane, the step of identifying at least one additional image file further includes the steps of comparing a distance between the first plane and the second plane to a threshold and identifying the at least one additional image file when the distance is less than the threshold. When the first plane is not parallel to the second plane, the step of identifying at least one additional image file includes the steps of determining a distance between the region of interest and a point in the second plane that is closest to the region of interest, comparing the distance to a threshold, and identifying the at least one additional image file when the distance is less than the threshold.

These and other advantages and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Various exemplary embodiments of the subject matter disclosed herein are illustrated in the accompanying drawings in which like reference numerals represent like parts throughout, and in which.

In describing the various embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terries similar thereto are often used. They are not limited to direct connection but include connection through other elements where such connection is recognized as being equivalent by those skilled in the art.

DETAILED DESCRIPTION OF THE INVENTION

The various features and advantageous details of the subject matter disclosed herein are explained more fully with reference to the non-limiting embodiments described in detail in the following description.

Figure 1:
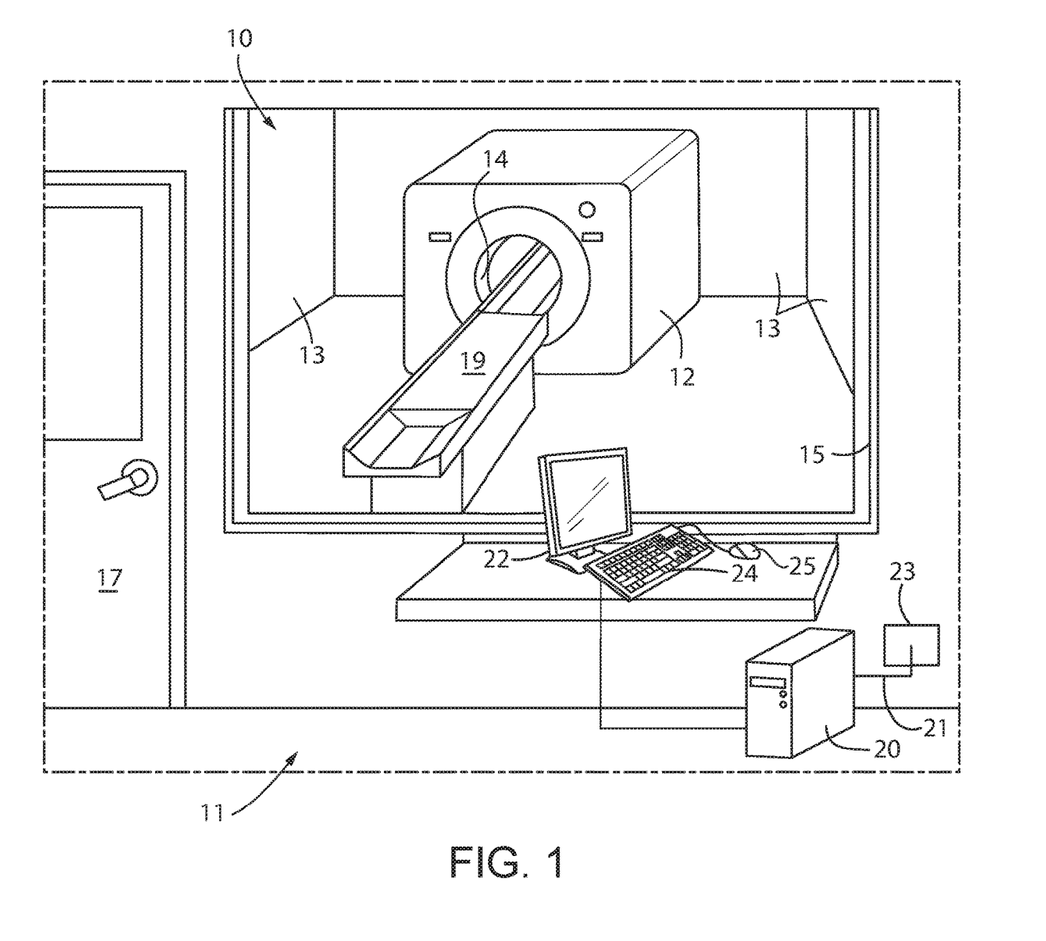
FIG. 1 is an exemplary embodiment of an MRI scan room.

Referring initially to FIG. 1, an exemplary medical imaging application including an MRI scanner 12 is illustrated. The MRI scanner 12 is located within a shielded room 10, or scan room. The scan room 10 includes walls 13, or panels, which typically incorporate RF shielding within the wall 13. A window 15 permits an operator to observe activity within the scan room 10 from an adjacent control room 11, typically connected via a door 17. The door 17 may similarly incorporate RF shielding within the solid portion of the door. The window 15 between the scan room 10 and the control room 11 and, if present, a window in the door 17 are covered in a conductive material such as a fine wire mesh or a thin metallic foil made, for example, from copper or gold to provide RF shielding on the window. The shielding is configured to prevent external RF signals that are in a spectrum that may interfere with the MRI scanner 12 from entering the scan room 10 and causing said interference.

A controller 20 for the MRI scanner 12 is typically located in the adjacent control room 11. A display device, for example, a monitor 22 or other display unit and a user interface such as a keyboard 24 and/or mouse 25 are connected to the controller 20. The controller 20 may be connected to the MRI scanner 12 by cabling extending, for example, under the floor of the scan room 10 or in a shielded conduit to the MRI scanner 12. A penetration panel 23 in the wall may also provide connections to cables 21 running from the controller 20 into the scan room 10. The penetration panel 23 may include connectors for cabling to other medical equipment present in the scan room 10. Corresponding connectors on the other side of the penetration panel 23 within the scan room 10 permit appropriately shielded cables to be connected and run to the scanner 12 or to other medical equipment.

Figure 2:
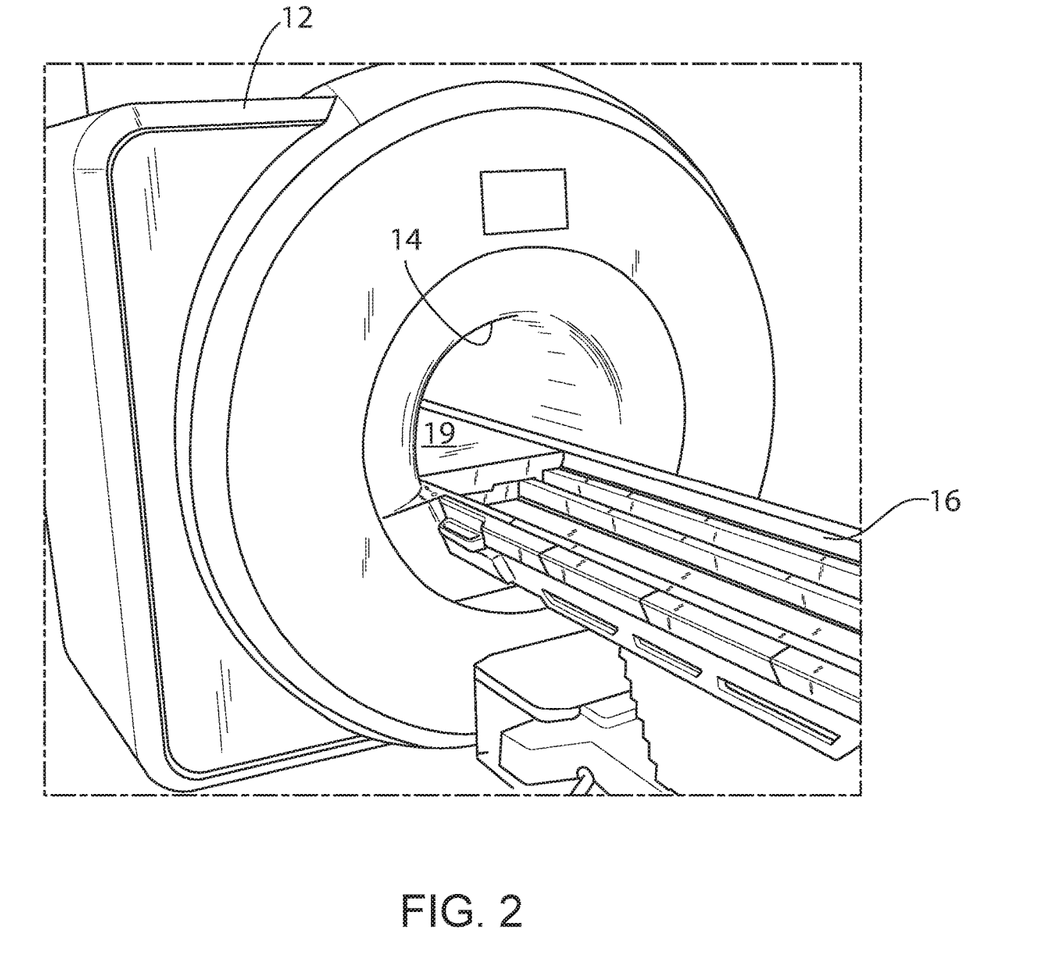
FIG. 2 is a pictorial view of an exemplary MRI scanner.
Figure 3:
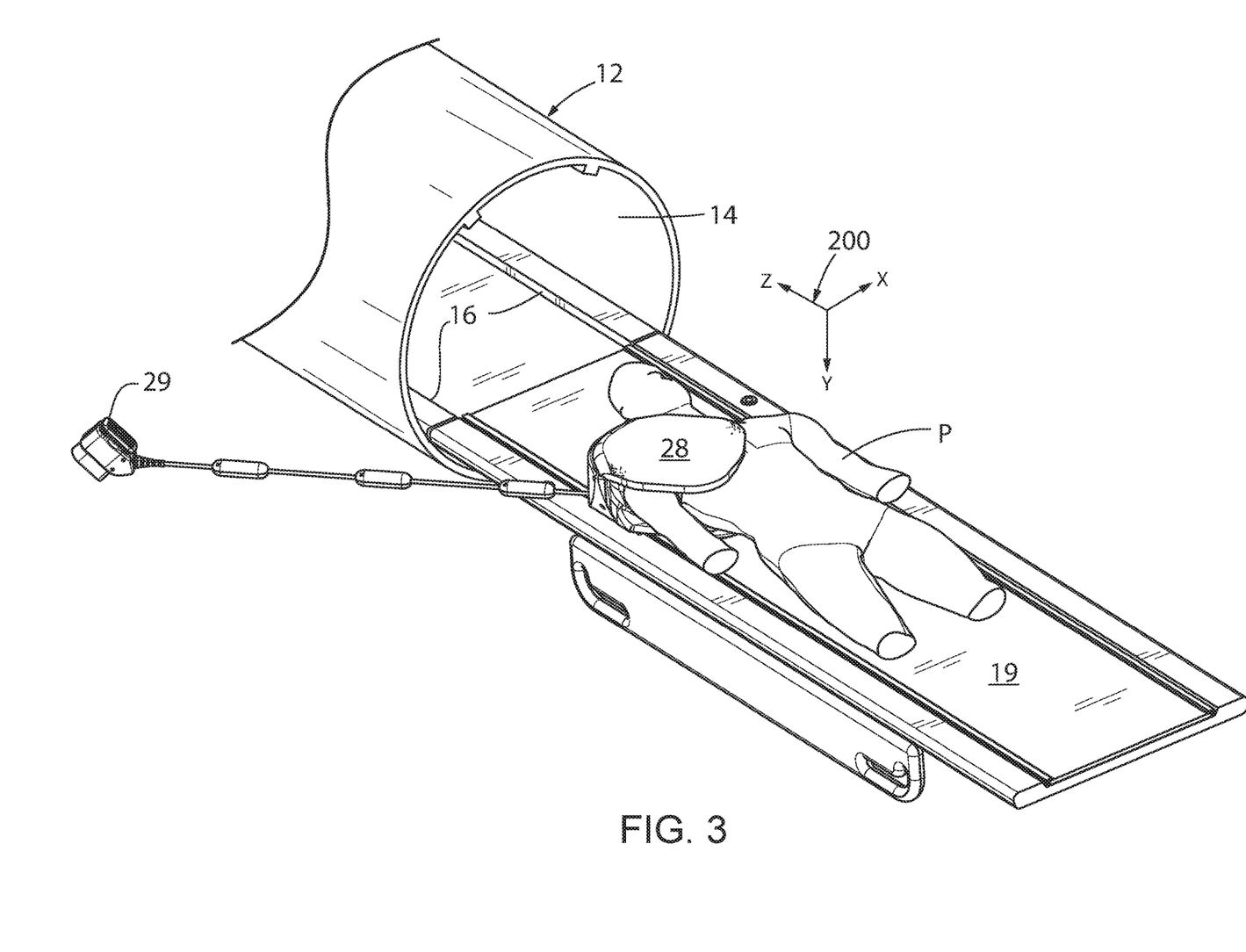
FIG. 3 is a perspective view of a patient on a scan table prior to entry into the bore of an MRI scanner.

With reference also to FIGS. 2 and 3, additional details of an exemplary MRI scanner 12 are illustrated. The MRI scanner 12 includes a bore 14 in which a patient, P, is positioned during imaging. Prior to imaging, the patient, P, is initially positioned on a scan table 19 external to the bore 14. An MIDI coil 28, or antenna array, used to detect the NMR signals the from an anatomical region of interest is positioned on the patient, P. According to the illustrated embodiment, the patient, P, is positioned on a shoulder coil 28 on the table 19. The shoulder coil 28 includes a plug 29 which is connected to the scanner 12 and transmits the detected NMR signals to the scanner. The shoulder coil 28 is an exemplary MRI coil. Various other coils and/or multiple coils may be utilized during a scan, where each coil may take various shapes and forms according to the anatomical region of interest during a scan. Once a patient, P, is positioned on the table 19 external from the bore, the table 19 may be slid into the bore along rails 16 extending along each side of the table.

Figure 4:
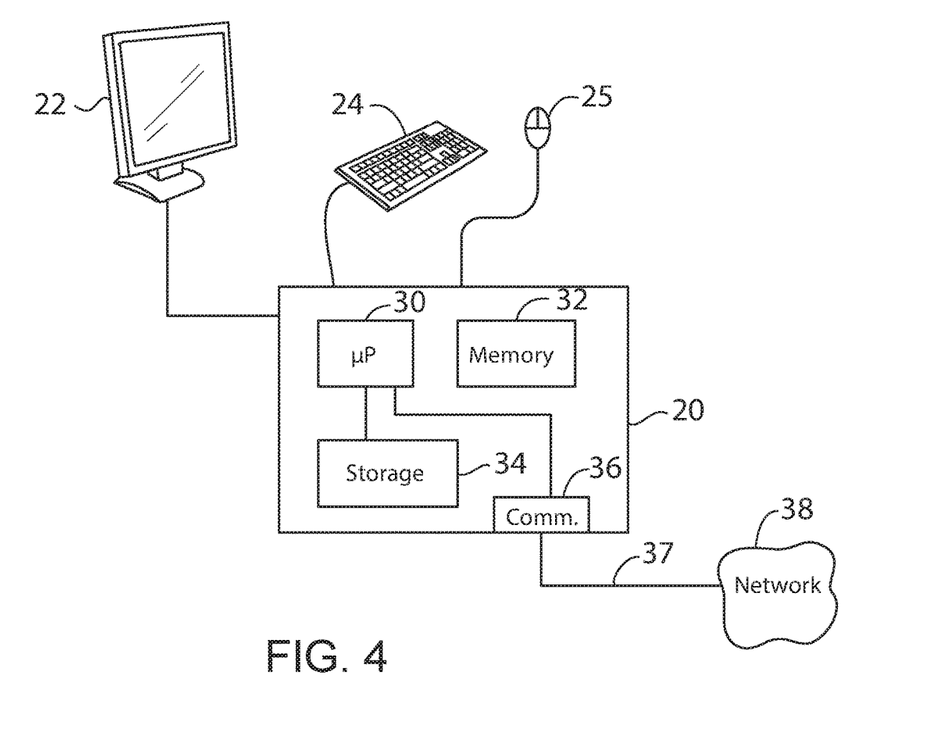
FIG. 4 is a block diagram representation of an exemplary controller for the MRI scanner of FIG. 1.

Turning next to FIG. 4, a block diagram representation of the controller 20 is illustrated. The controller 20 includes a processor 30 in communication with a memory 32. It is contemplated that the processor 30 may be a single microprocessor, multiple microprocessors operating in tandem, a general-purpose microprocessor and a dedicated co-processor utilized, for example, for mathematical computations or graphical processing, or a combination thereof. The memory 32 may include transitory memory, non-transitory memory, or a combination thereof and may be implemented on a single device or on multiple devices. At least one user interface and at least one display device 22 is connected to the controller 20, The illustrated embodiment includes a keyboard 24, a mouse 25, and a single monitor. It is contemplated that various other user interfaces may be included, such as a trackball, joystick, touchpad, touchscreen and the like. Similarly, multiple monitors may be connected to the controller 20 without deviating from the scope of the invention.

The controller 20 may further include one or more storage devices 34. The storage device 34 may be configured to store applications which may be executed on the controller 20 by the processor 30. The storage device may be further configured to store image data obtained from the imaging process. According to one aspect of the invention, the image data may be stored according to the Digital Imaging and Communications in Medicine (DICOM) standard for handling, storing, retrieving, printing, and transmitting data in medical imaging. The storage device 34 may be a local, fixed storage device, such as a magnetic disk drive, an optical disk drive, or a solid-state disk drive. The storage device 34 may also be a local, removable storage device including, but not limited to, a Universal Serial Bus (USB) drive, a memory card, or an optical disk, such as a compact disk (CD) or digital video disk (DVD). Optionally, a storage device 34 may be located remotely from the controller 20 where the controller 20 may be in communication with the storage device via a network 38 and any suitable communication interface 36 and network hardware 37 including, but limited to, network cabling, gateways, switches, routers, and the like. The network 38 may include wired devices, wireless devices, or a combination thereof. The remote storage device 34 may include a server located in another location within the facility or in a remote facility or, optionally, may include cloud storage. It is further contemplated that multiple storage devices 34 having various combinations of the above-mentioned devices may be included.

In operation, one or more MRI coils 28 are selected according to the examination requirements and positioned along with the patient, P, on the table 19 prior to being loaded into the bore 14 of the MRI scanner 12. A scanning protocol is established during which a series of scans of the patient are defined. One or more initial scans may be performed to calibrate the MRI scanner 12, define a coordinate system, establish a reference position between the anatomical region being imaged to a known location on the table 19, and the like. With reference again to FIG. 3, a coordinate system may be defined within the MRI scanner in which an origin of the coordinate system is present at the upper left position at the entrance of the bore 14. An X-axis extends in a positive direction from the right-to-left of the patient, P, positioned on the table 19, A Y-axis extends in a positive direction from the front-to-rear (anterior-to-posterior) of the patient, P, and a Z-axis extends in a positive direction from the feet-to-head (inferior-to-superior) of the patient. Various planes of imaging are defined with respect to the coordinate system, A sagittal plane is located in the Y-Z plane and separates the right and left sides of the patient. A coronal plane is located in the X-Z plane and separates the anterior and posterior sides of the patient. An axial plane is located in the X-Y plane and separates the inferior and superior portions of the patient. MRI coils 28 may be positioned within the bore 14 and in appropriate relationships with the patient, P, to obtain images in one or more of these planes during the various scans.

During some examinations, a patient may be inserted and removed from the bore multiple times, for example, to utilize different MRI coils 28 during different scans. When the patient is inserted into the bore for the first set of scans, an initial scan may identify a particular location on the patient as a reference point. The coordinates of the reference point and as well as a relationship to the table 19 and/or the coordinate system for the MRI scanner 12 may be stored. For each image obtained during the first set of scans, both pixel data, corresponding to the anatomical region of interest, and location information, defining a relationship of the pixel data to the reference point, is stored. After the first set of scans, the patient, P, may be removed from the bore 14. The patient, P, and the associated MRI coils 28 may be reconfigured for a subsequent set of scans. When the patient is reinserted into the bore for the subsequent set of scans, another scan may be performed to identify the particular location on the patient used as a reference point. The coordinates of the reference point and as well as a new relationship to the table 19 and/or the coordinate system for the MRI scanner 12 may be stored. For each additional scan or set of scans, both pixel data, corresponding to the anatomical region of interest, and location information, defining a relationship of the pixel data to the reference point, is again stored. Utilizing the correlation of the reference point to the MRI scanner coordinates allows images obtained during different scans between which a patient may move or be moved on the table 19 to be compared to each other.

In one embodiment of the invention, the coordinate information for each image is stored along with the pixel data for the image in a single data file. Optionally, a data file may contain multiple images where each image is referenced to a single location. According to still another option, a data file may include multiple images where each image includes separate coordinate information for each image as well as separate reference data correlating the coordinate information for each image to the MRI scanner coordinate system. In yet another embodiment of the invention, it is contemplated that the pixel data for each image may be stored in image files while the coordinate information may be stored in a separate file. A single file may include, for example, a data table with coordinate information for each image as well as a correspondence between the coordinate information for the image and the MRI scanner coordinate system. It is contemplated that various data structures may be utilized to store pixel information and coordinate information for the corresponding pixel information without deviating from the scope of the invention.

Figure 5:
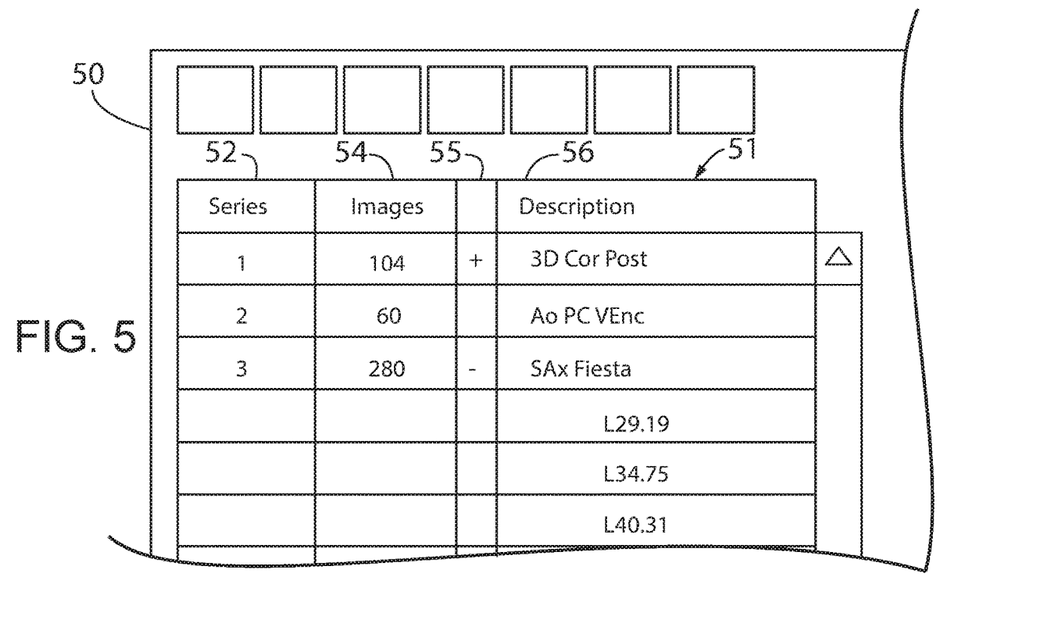
FIG. 5 is a partial screen capture of an application incorporating a system for displaying medical images according to one embodiment of the invention.

During an examination, a scanning protocol is established defining the number and type of scans to be performed on the patient for the exam. Each scan includes multiple images and may be defined by a different set of parameters. The parameters may relate, for example, to image resolution, orientation of the anatomical region being imaged, image contrast, scan rate, pulse sequence, or the like. Further, multiple images of the same region may be obtained at different instances in time with a defined interval between each image. The images may be displayed in a movie mode, where each image is sequentially displayed at the defined interval to provide information, for example, on a moving organ such as the heart. The sets of images may be stored as a series on the scanner or on an external computer for subsequent analysis and review. Each series may include just a few images (e.g. 10 or less) or up to hundreds of images. With reference to FIG. 5, a screen shot 50 of an exemplary analysis application executing on the controller 20 provides a menu 51 of the different series 52 stored on the storage device 34. The menu 51 identifies the number of images 54 present in each series 52 and a description 56 of each series. An expansion column 55 in the menu 51 may be used to open or close each series 52. When a series 52 is open, such as the third series in the illustrated example, descriptions of individual images are provided in a list and may be selected for display.

Figure 6:
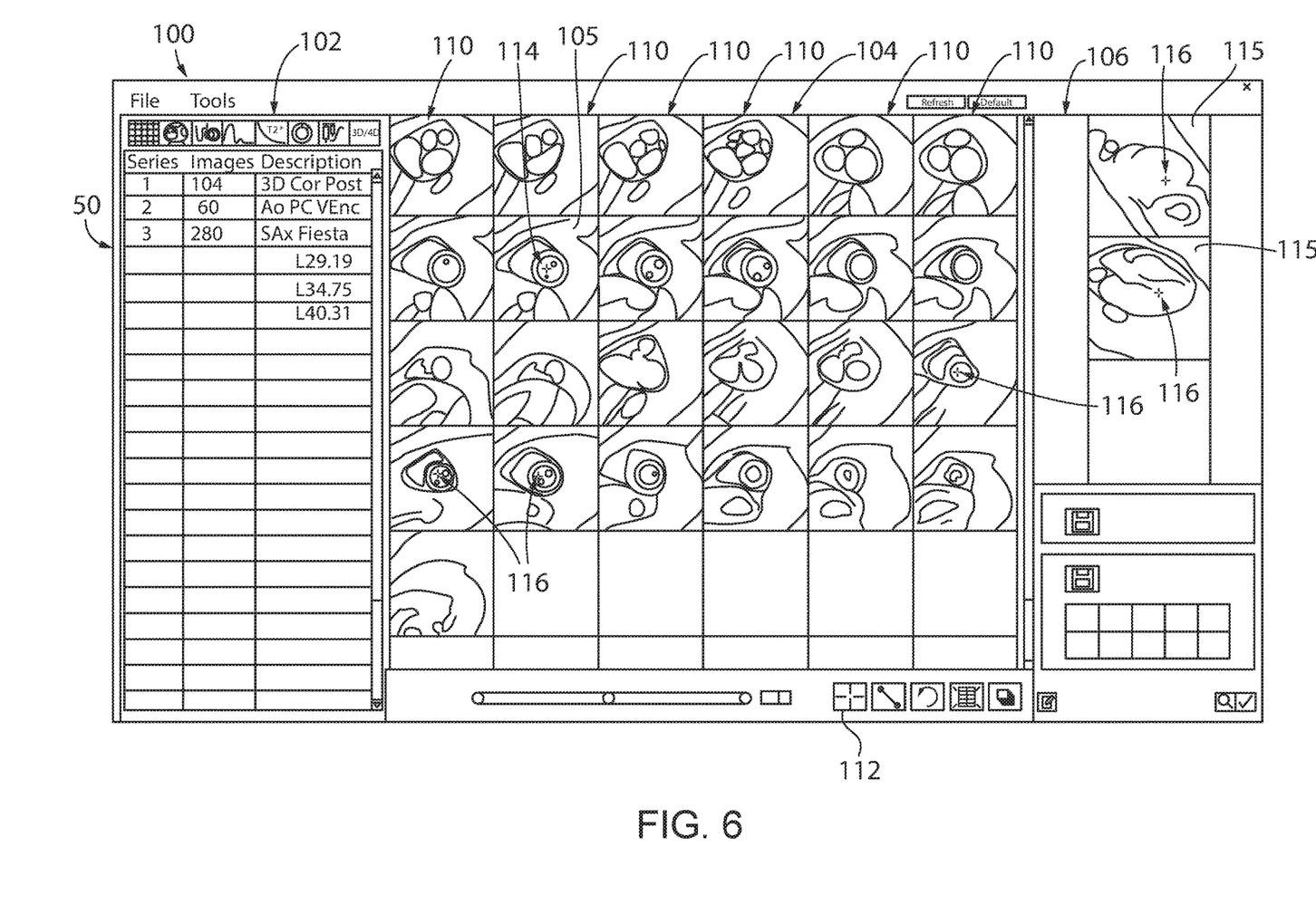
FIG. 6 is a screen capture of the application of FIG. 5.
Figure 7:
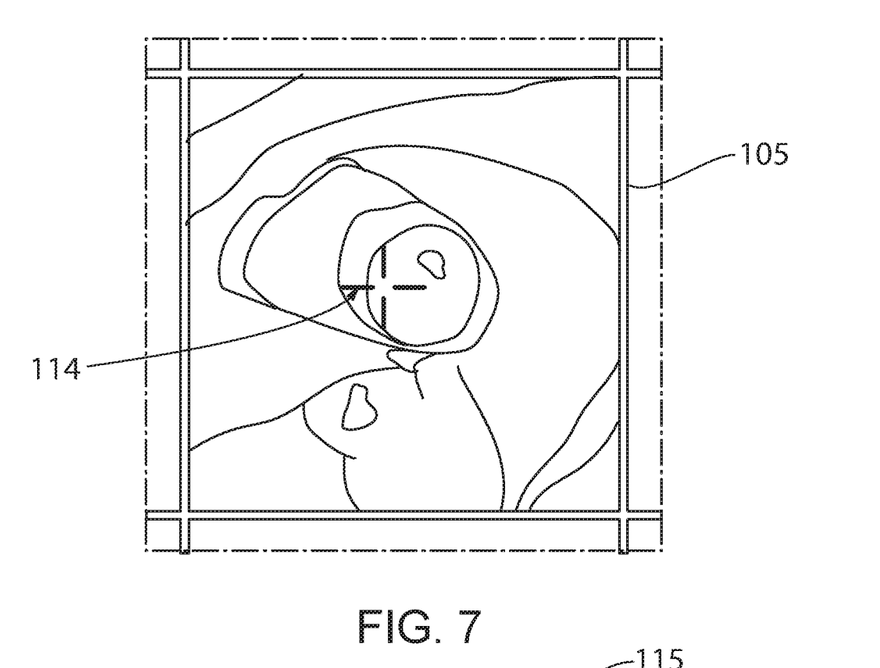
FIG. 7 is a partial view of the screen capture of FIG. 6 illustrating selection of a point of interest in an initial image.
Figure 8:
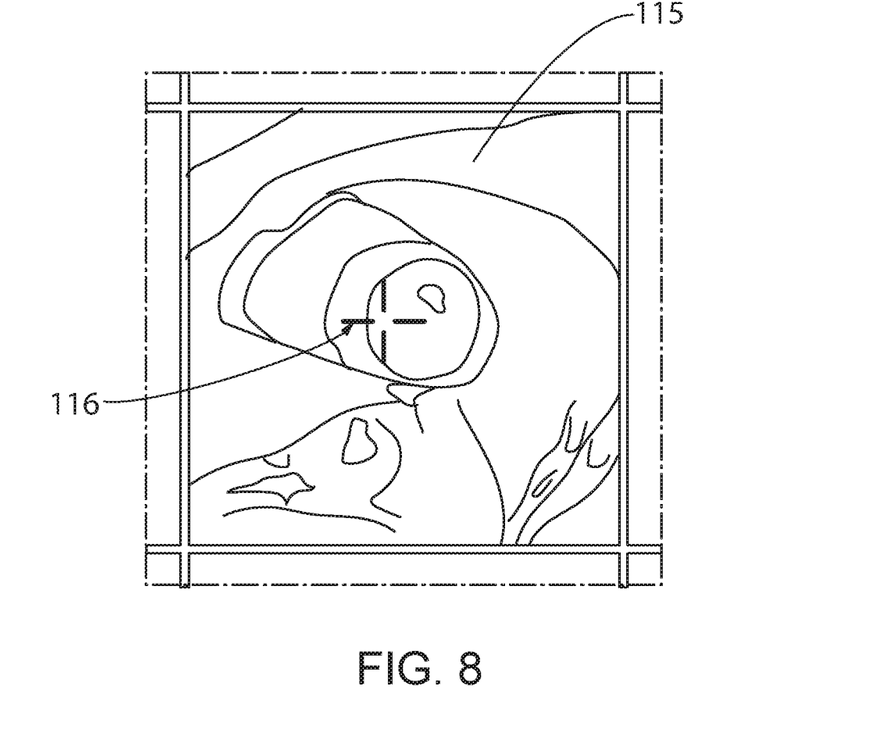
FIG. 8 is a partial view of the screen capture of FIG. 6 illustrating identification of the selected point in an additional image.

Upon completion of an examination and when all of the series and the corresponding images are stored, a technician must review each of the stored images in order to provide a diagnosis of the patient. Turning next to FIG. 6, a screen shot 100 of an exemplary application executing on the controller 20 may be used to display and review various images 110 obtained during the examination. In the illustrated embodiment, the left side 102 of the screen shot includes the menu 51 discussed above with respect to FIG. 5. A center portion 104 of the screen displays images 110 in a grid format. It is contemplated that the number of rows and columns in the grid are selectable by the technician such the number and size of images 110 displayed at one time may be changed by the technician. For instance, it may be desirable to initially display a large number of images with a smaller size for each image in the center portion for a brief review of the images. Having identified one or more images for further inspection, the technician may reduce the number of images displayed, allowing each image to be larger in size for improved viewing. A right side 106 of the screen may be used to select specific images for further review. Various other configurations of an application may be utilized to display images to the technician without deviating from the scope of the invention.

Figure 9:
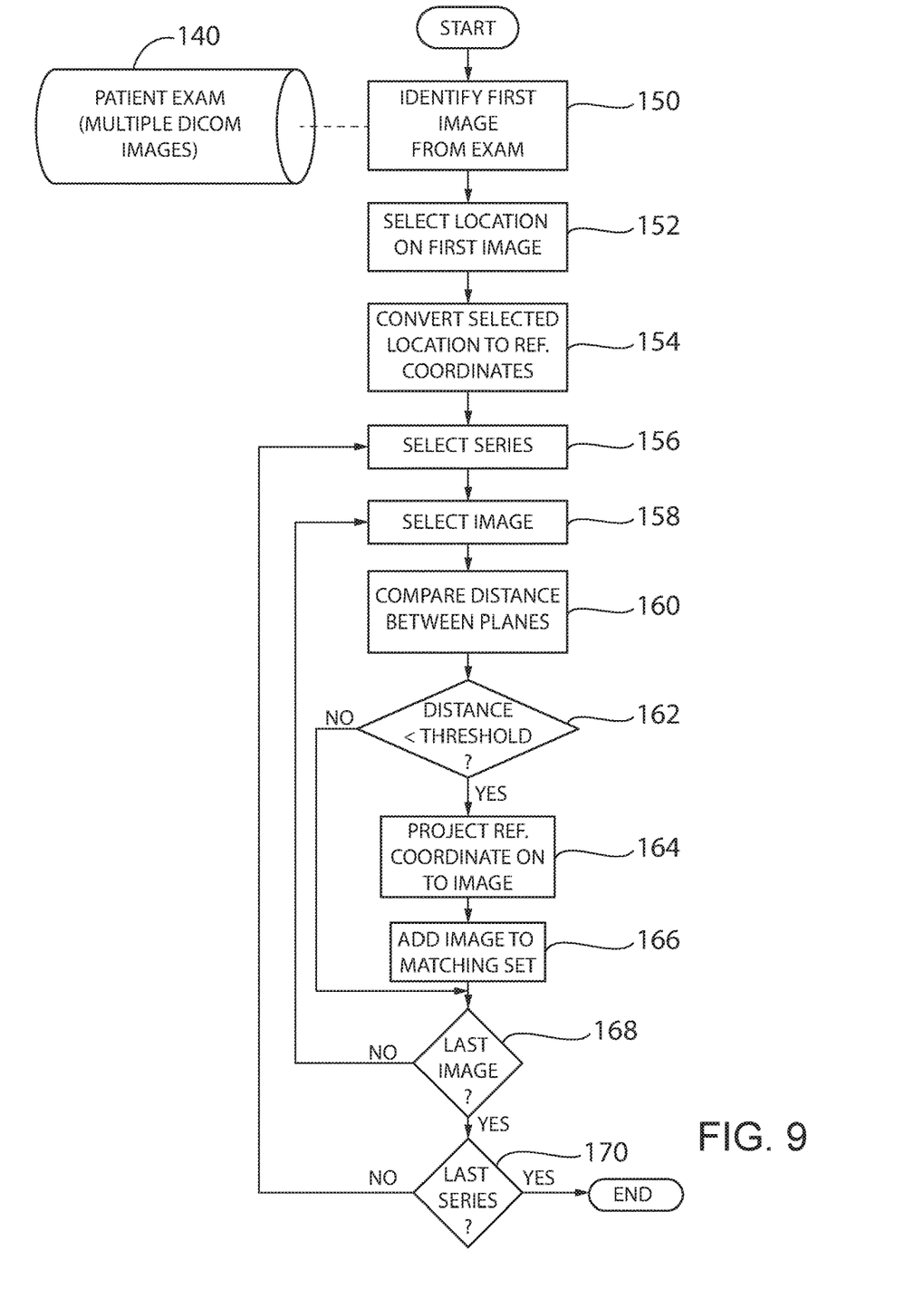
FIG. 9 is a flow diagram of a method for identifying and displaying medical images according to one embodiment of the invention.

With reference next to FIG. 9, a flow diagram illustrates steps in a process for identifying regions of interest within an image and for locating additional images containing the region of interest, A set of images 140 is stored on the storage device 34 and is being reviewed by a physician. At step 150, the physician identifies a first image from the set of images 140 that includes a region of interest. With reference also to FIG. 6, the first image 105 may be any image within the set of images 140 and may not be the initial image viewed by the physician during the review of the images obtained during the patient examination. Rather, the first image 105 is an image in which the region of interest is initially identified.

At step 152, the physician identifies a location on the first image. With reference again to FIG. 6, the application may include a selection tool 112, where the selection tool 112 is identified in the exemplary screen shot 100 as a crosshair within a box at the bottom of the screen shot 100. The selection tool 112 may be a button which, in turn, presents a cursor in the form of the crosshair on the display screen. The physician may position the cursor on the screen via any suitable user interface such as the mouse 25, a touch screen, a touch pad, a track ball, a joystick, or the like until the center of the crosshair is located over the region of interest in the first image 105. The physician then indicates the crosshair is at the desired location via the user interface, for example, by pressing a button on the mouse 25, pressing enter on the keyboard 24, or via any other suitable indication from the user interface. The identified location 114 is shown on the first image 105 by the appearance of a crosshair or any other suitable location indicia. It is also contemplated that steps 150 and 152 may be performed in tandem, where identification of the first image is performed by selecting a location on the image.

Once the identified location 114 has been selected in the first image, the coordinates of the location are converted to a reference set of coordinates as indicated in step 154. The identified location 114 on the two-dimensional image is translated to the reference coordinate system established for the examination. With reference again to FIG. 3 and with further reference to FIG. 10, the Cartesian coordinate system 200 and the origin 202 defined for the Cartesian coordinate system 200 serve as a reference coordinate system. As discussed above, the coordinate information defining a relationship between the pixel data in each image and the reference coordinate system 200 is stored for each set of pixel data. In one embodiment of the invention, the pixel data and the coordinate information are stored in a single data file according to DICOM format. The coordinate information may be defined by a first value defining the location of the image and a second value defining an orientation of the image. The location of the image may be defined by an image origin 210 according to the reference Cartesian coordinate system 200 and include an X-axis, Y-axis, and Z-axis position for the upper, left-hand corner of the image. An additional offset 222 from the upper, left-hand corner may be defined according to the exact position 220 within the first image 105 at which the identified location 114 is located. The offset 222 may be determined according to a particular pixel identified within the first image 105, according to a pixel spacing defining the distance, as a function of the reference coordinate system, between pixels in each row and column of the image, and according to a distance that the pixel is from the image origin 210. Further, the orientation information for the image defines the directions within the coordinate system at which the first row 212 and the first column 214 of the image extends. Thus, the orientation information defines the direction the plane 215 of the 2D image extends from the image origin 210 in the reference coordinate system 200. The offset 222, in combination with the image origin 210 and the orientation information, defines a particular location within the reference coordinate system 200 at which the region of interest is located.

Figure 10:
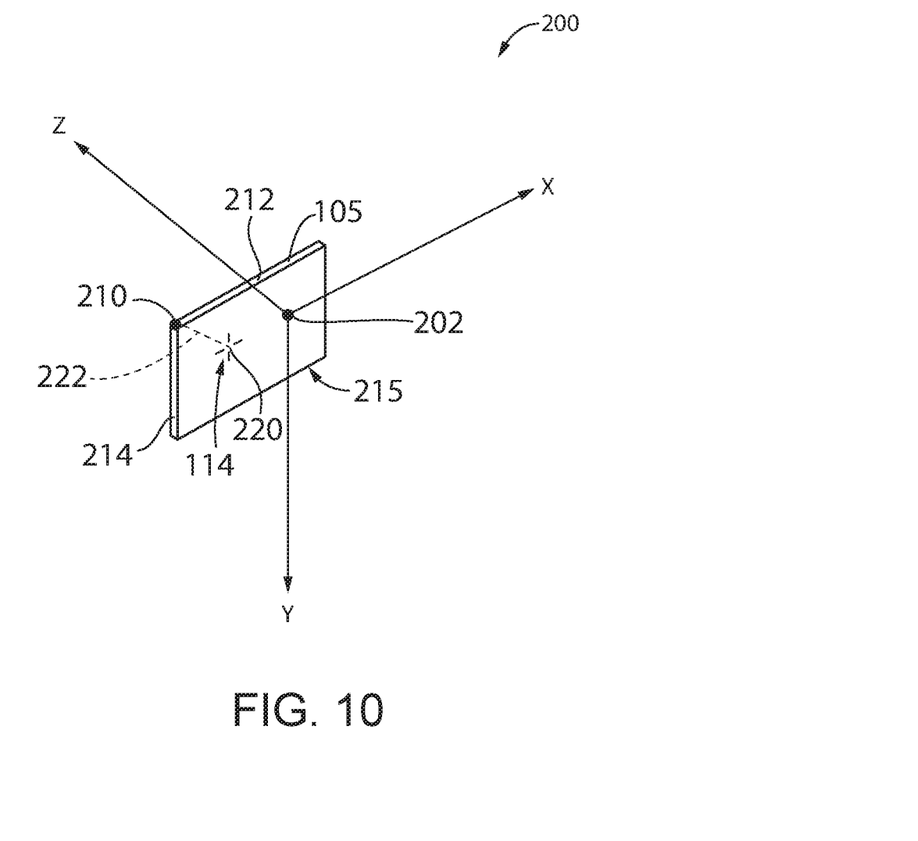
FIG. 10 is a graphical representation of one two-dimensional image located within a three-dimensional coordinate system.

Once the particular location within the reference coordinate system 200 at which the region of interest is located is identified, the controller 20 automatically identifies each of the other images 110 within a candidate set of images that contains the same location. It is contemplated that the candidate set of images may be the entire set of images 140 from the patient exam. Optionally, the candidate set of images may be a subset of the entire set of images 140 from the exam. The subset may include, for example, only additional images within an open series that the physician is presently reviewing. Optionally, one or more series of images may be highlighted in the menu and only the highlighted series may be included in the candidate set of images. According to still another aspect of the invention, an additional column may be added to the menu, where the additional column includes a check box or radio button for selection of the series for inclusion in the candidate set of images. Still other methods of identifying which images are included in the candidate set of images may be utilized without deviating from the scope of the invention.

A sequence is used to step through each image 110 in the candidate set of images. The exemplary set of images 140 are stored as multiple series of images where each series includes a varying number of images. Therefore, steps 156 and 158 are used to identify a first series and a first image from the series in which the controller 20 determines whether the identified location 114 is present. A distance between the identified location 114 in the first image and the position information corresponding to the additional image is determined. At step 160, the distance being determined is a distance between the plane defined in the first image 105 and a distance between the plane of the additional image. Optionally, it is contemplated that a point in the plane of the additional image that is closest to the identified location 114 may be determined and the distance between the closest point and the identified location 114 may be determined. At step 162, the determined distance (e.g., distance between planes or distance between points) is compared to a threshold. It is contemplated that the threshold may be a user defined parameter stored in the memory 32 of the controller. It is contemplated that the threshold may be set within a range of 1-20 min to indicate that the additional image intersects the identified location 114 within an acceptable distance to be considered of interest to the physician. It is further contemplated that the threshold may be adjusted according to an imaging parameter, such as the thickness of a slice or the separation between slices. If the slice thickness or separation between slices increases, the threshold may similarly increase such that the controller is able to identify a matching plane within the acceptable range. Conversely, if the slice thickness or separation between slices decreases, the threshold may similarly decrease such that the number of images falling within the acceptable range does not increase to such an extent that too many matching images are identified to be useful to the physician. According to yet another aspect of the invention, it is contemplated that the threshold may vary in different directions. For example, an image it may be desirable to have a first threshold for images that are located in a second plane that is parallel to the plane of the first image while having a second threshold for images that are located in a second plane that is perpendicular to the plane of the first image.

If the determined distance between the first image and the additional image exceeds the threshold, the controller 20 selects a new additional image for comparison. At step 168, the controller 20 first determines whether the current image being analyzed is the last image in a series. If not, the controller 20 may increment to the next image in the series and return to step 158, selecting the next image in the series.

If the current image being analyzed is the last image in a series, the controller 20 may reset the image number to the first image and move down to step 170. At step 170, the controller 20 first determines whether the current series being analyzed is the last series in the candidate set of images being reviewed. If not, the controller 20 may increment to the next series in the candidate set of images and return to step 156. There the controller 20 will identify the next series and, at step 158, the first image from the next series will be selected. If the series was the last series in the candidate set of images being reviewed, the controller 20 may reset the series to the first series and end the automatic identification routine. When the automatic identification routine is next run, the series and image will have been reset to the first series and the first image of the next candidate set of images to be analyzed.

If, however, the determined distance between the first image and the additional image is less than the threshold, the controller 20 moves down to steps 164 and 166. The additional image is considered to include the identified location 114 and is included in a set of images to present to the physician. At step 164, the identified location 114 is projected onto the additional image as a matching location 116. At step 166 the additional image is added to a set of matching images 115. According to one aspect of the invention, the set of matching images 115 may be a new series of images in which each additional image and the matching location information is stored. According to another aspect of the invention, each matching image 115 may be displayed on the display device 22 along with the matching location 116 for the physician to compare against the identified location 114 in the first image 105. After identifying the matching location 116 and providing an indication to the physician of the additional image and the location corresponding to the originally identified location, the controller 20 may proceed to the next additional image in a manner discussed above and as shown in steps 168 and 170.

Although the sequence for identifying regions of interest within an image and for locating additional images containing the region of interest are discussed above with respect to the controller 20. It is contemplated that the set of images 140 may be stored on a server via the network 38 and accessed by another computing device connected to the server via the network 38. The other computing device may be, for example, in a separate office at the same facility or in a location remote from the facility at which the scanning is performed. Optionally, the set of images 140 may be transferred to the other computing device via a removable storage medium. The sequence of steps discussed above may be executed on the other computing device without deviating from the scope of the invention.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A method for displaying images obtained from a magnetic resonance imaging (MRI) scanner, the method comprising the steps of:
   displaying a first image of an anatomical region obtained from the MRI scanner on a display device;
   receiving an input at a processor from a user interface, wherein the input defines a position within the first image;
   reading a data set from a storage device in communication with the processor, wherein:
      the data set corresponds to the first image,
      the data set is stored within an image file for the first image, and
      the data set includes coordinate information for a location of the anatomical region during imaging;
   determining the location for the anatomical region during imaging from the data set that corresponds to the position within the first image defined by the input; and
   identifying at least one additional image of the anatomical region which includes the location of the anatomical region that corresponds to the position within the first image, wherein:
   each additional image is stored in an additional image file,
   each additional image file includes coordinate information for the corresponding additional image, and
   the step of identifying the at least one additional image of the anatomical region further comprises the steps of:
      reading the coordinate information from each additional image file;
      comparing the location of the anatomical region that corresponds to the position within the first image to the coordinate information from each additional image file; and
      identifying the at least one additional image when the coordinate information from a corresponding additional image file includes the location of the anatomical region that corresponds to the position within the first image.

2. A method for displaying images obtained from a magnetic resonance imaging (MRI) scanner, the method comprising the steps of:
   displaying a first image of an anatomical region obtained from the MRI scanner on a display device;
   receiving an input at a processor from a user interface, wherein the input defines a position within the first image;
   reading a data set from a storage device in communication with the processor, wherein:
      the data set corresponds to the first image,
      the first image is stored in an image file,
      the data set is stored within a separate file from the image file, and
      the data set includes coordinate information for a location of the anatomical region during imaging;
   determining the location for the anatomical region during imaging from the data set that corresponds to the position within the first image defined by the input and
   identifying at least one additional image of the anatomical region which includes the location of the anatomical region that corresponds to the position within the first image, wherein:
      each additional image is stored in an additional image file,
      the separate file includes coordinate information for each additional image, and the step of identifying the at least one additional image of the anatomical region further comprises the steps of:
  reading the coordinate information from the separate file for each additional image;
  comparing the location of the anatomical region which corresponds to the position within the first image to the coordinate information for each additional image; and
  identifying the at least one additional image when the coordinate information for the additional image includes the location of the anatomical region which corresponds to the position within the first image.

3. The method of claim 1 further comprising the step of displaying each additional image on the display device with the first image.

4. The method of claim 1 further comprising the step of providing a list of each additional image identified on the display device.

5. A system for displaying images obtained from a magnetic resonance imaging (MRI) scanner, the system comprising:
  a storage device configured to store a plurality of images of an anatomical region obtained from the MRI scanner and a data set corresponding to the plurality of images, wherein the data set is stored within a plurality of image files and wherein each image file includes one of the plurality of images and coordinate information for the corresponding image;
  a display device configured to selectively show each of the plurality of images;
  a user interface configured to generate a signal corresponding to a position within a first image shown on the display device, wherein the first image is selected from the plurality of images;
  a processor operative to receive the signal from the user interface and, responsive to the receiving the signal, the processor is further operative to:
    read the data set from the storage device, wherein the data set includes coordinate information for a location of the anatomical region during imaging for each of the plurality of images;
    determine the location for the anatomical region during imaging from the data set that corresponds to the position within the first image defined by the signal; and
    identify at least one additional image of the anatomical region which includes the location of the anatomical region that corresponds to the position within the first image, wherein the at least one additional image is selected from the plurality of images, and wherein:
      identifying the at least one additional image of the anatomical region further comprises:
        reading the coordinate information for each additional image from the corresponding image file;
        comparing the location of the anatomical region that corresponds to the position within the first image to the coordinate information for each additional image; and
        identifying the at least one additional image when the coordinate information for the additional image includes the location of the anatomical region that corresponds to the position within the first image.

6. A system for displaying images obtained from a magnetic resonance imaging (MM) scanner, the system comprising:
  a storage device configured to store a plurality of images of an anatomical region obtained from the MRI scanner and a data set corresponding to the plurality of images, wherein each of the plurality of images is stored in an image file and the data set is stored within a separate file from the image files;
  a display device configured to selectively show each of the plurality of images;
  a user interface configured to generate a signal corresponding to a position within a first image shown on the display device, wherein the first image is selected from the plurality of images;
  a processor operative to receive the signal from the user interface and, responsive to the receiving the signal, the processor is further operative to:
    read the data set from the storage device, wherein the data set includes coordinate information for a location of the anatomical region during imaging for each of the plurality of images;
    determine the location for the anatomical region during imaging from the data set that corresponds to the position within the first image defined by the signal; and
    identify at least one additional image of the anatomical region which includes the location of the anatomical region that corresponds to the position within the first image, wherein the at least one additional image is selected from the plurality of images, and wherein:
      identifying the at least one additional image of the anatomical region further comprises:
        reading the coordinate information from the separate file for each additional image;
        comparing the location of the anatomical region which corresponds to the position within the first image to the coordinate information for each additional image; and
        identifying the at least one additional image when the coordinate information for the additional image includes the location of the anatomical region which corresponds to the position within the first image.

7. A method for displaying images obtained from a magnetic resonance imaging (MRI) scanner, the method comprising the steps of:
  reading pixel data from a first image file, wherein the first image file corresponds to an anatomical region being imaged by the MRI scanner;
  displaying the pixel data on a display device;
  selecting a pixel from the pixel data displayed on the display device via a user interface, wherein the pixel defines a region of interest;
  reading position information from the first image file, wherein the position information includes coordinate information which defines a location of the pixel data with respect to a reference coordinate system;
  determining the location of the pixel within the reference coordinate system as a function of the coordinate information; and
  reading coordinate information for at least one additional image file, wherein the at least one additional image file includes an additional image having pixel data that corresponds to the location of the region of interest;
  comparing the location of the pixel selected from the first image file to the coordinate information for the at least one additional image file; and identifying the at least one additional image file when the coordinate information for the at least one additional image file matches the coordinate information position of the pixel selected from the first image file.

8. The method of claim 7 wherein the position information includes an image origin and an orientation of the pixel data within the reference coordinate system.

9. The method of claim 8 wherein the step of determining the location of the pixel within the reference coordinate system further includes the steps of:
   determining an offset of the pixel within the pixel data from the image origin as a function of the orientation of the pixel data within the reference coordinate system; and
   adding the offset to the image origin to determine the location of the pixel.

10. The method of claim 8 wherein each additional image file includes pixel data and position information corresponding to the additional image.

11. The method of claim 10 wherein the orientation of the first image file and the orientation of the at least one additional image file indicate that the pixel data in the first image file is in a first plane parallel to a second plane, wherein the second plane includes the pixel data in the second image and wherein the step of identifying at least one additional image file includes the steps of:
   comparing a distance between the first plane and the second plane to a threshold; and
   identifying the at least one additional image file when the distance is less than the threshold.

12. The method of claim 10 wherein the orientation of the first image file and the orientation of the at least one additional image file indicate that the pixel data in the first image file is in a first plane that is not parallel to a second plane, wherein the second plane includes the pixel data in the second image and wherein the step of identifying at least one additional image file includes the steps of:
   determining a distance between the region of interest and a point in the second plane that is closest to the region of interest;
   comparing the distance to a threshold; and
   identifying the at least one additional image file when the distance is less than the threshold.

13. The method of claim 7 further comprising the step of displaying the pixel data from each additional image file on the display device with the pixel data from the first image file.

* * * * *